United States Patent [19]

Ono et al.

[11] Patent Number: 4,885,400
[45] Date of Patent: Dec. 5, 1989

[54] PRODUCTION PROCESS OF 2-CHLOROPROPIONALDEHYDE

[75] Inventors: Hiroshi Ono; Takaharu Kasuga, both of Kanagawa, Japan

[73] Assignee: Mitsui Toatsu Chemicals, Incorporated, Tokyo, Japan

[21] Appl. No.: 145,759

[22] PCT Filed: May 20, 1987

[86] PCT No.: PCT/JP87/00320
§ 371 Date: Dec. 1, 1987
§ 102(e) Date: Dec. 1, 1987

[87] PCT Pub. No.: WO87/07262
PCT Pub. Date: Dec. 3, 1987

[30] Foreign Application Priority Data

May 20, 1986 [JP] Japan .................... 61-113543
May 20, 1986 [JP] Japan .................... 61-113545
May 22, 1986 [JP] Japan .................... 61-116140

[51] Int. Cl.$^4$ .................................... C07C 45/50
[52] U.S. Cl. .................................... 568/454; 568/451; 568/455; 568/466
[58] Field of Search ............... 568/451, 454, 455, 466

[56] References Cited

U.S. PATENT DOCUMENTS

| 3,239,570 | 3/1966 | Slaugh et al. | 568/454 |
| 4,654,445 | 3/1987 | Ono et al. | 568/454 |
| 4,740,626 | 4/1988 | Bahrmann et al. | 568/454 |

FOREIGN PATENT DOCUMENTS

| 183199 | 6/1986 | European Pat. Off. | 568/455 |
| 216315 | 4/1987 | European Pat. Off. | 568/455 |
| 1397779 | 3/1965 | Japan | 568/454 |
| 45-9730 | 4/1970 | Japan | 568/454 |
| 45-10729 | 4/1970 | Japan | 568/454 |
| 59-95239 | 1/1984 | Japan | 568/454 |
| 61-126046 | 6/1986 | Japan | 568/454 |
| 62-10038 | 1/1987 | Japan | 568/454 |
| 62-22738 | 1/1987 | Japan | 568/454 |

Primary Examiner—Werren B. Lone
Attorney, Agent, or Firm—Fisher, Christen & Sabol

[57] ABSTRACT

In the production of 2-chloropropionaldehyde by the hydroformylation of vinyl chloride in the presence of a rhodium catalyst in combination with a base, the activity of the catalyst can be improved significantly by maintaining the concentration of produced 2-chloropropionaldehyde in the reaction solution at not higher than 10%.

Further, it is possible to continue the reaction for a long period of time while maintaining the activity of the catalyst at a high level by carrying out the reaction in a water insoluble or hardly soluble solvent simultaneously with water extraction, separating the catalyst solution and the extraction water from each other, separating 2-chloropropionaldehyde from the extraction water by distillation or similar means so as to lower its concentration to a given level or below, and using the extraction water again after subjecting it to an anion exchange treatment.

1 Claim, 1 Drawing Sheet

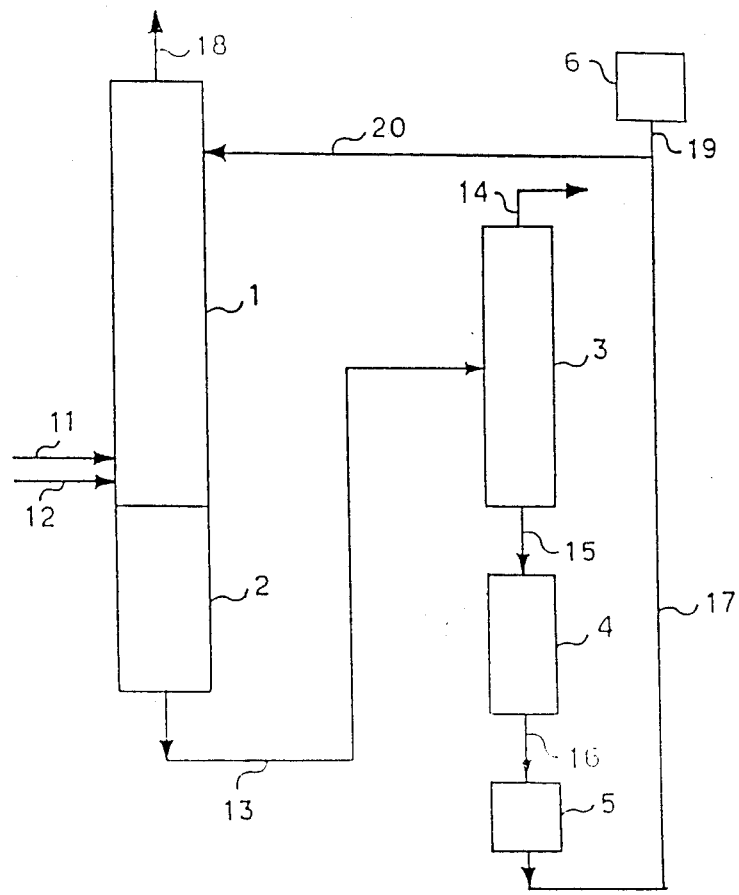

PRODUCTION PROCESS OF 2-CHLOROPROPIONALDEHYDE

TECHNICAL FIELD

This invention relates to an improved process for the production of 2-chloropropionaldehyde from vinyl chloride, carbon monoxide and hydrogen.

BACKGROUND ART

2-Chloropropionaldehyde can find applications as useful intermediates for chemicals, agricultural chemicals and medicines. It has been known to produce this compound from vinyl chloride, carbon monoxide and hydrogen as raw materials, as disclosed, for example, in French Patent No. 1,397,779 and HELVETICA CHIMICA ACTA, 48(5), 1151–1157. All of these processes employ cobalt carbonyl as a catalyst In French Patent No. 1,397,779 referred to above, for example, the raw materials are reacted for 90 minutes under the conditions of a reaction temperature of 110° C. and a reaction pressure of 200 atm., thereby obtaining reaction results of a vinyl chloride conversion of 57.4% and a selectivity to 2-chloropropionaldehyde of 86.2%

However, these processes which employ cobalt carbonyl as a catalyst require cobalt carbonyl in a large amount and a reaction pressure as high as 160–200 atm. because the catalytic activity per unit amount of cobalt is extremely low. Moreover, the reaction is carried out at a reaction temperature of 75°–125° C. for 90–120 minutes.

The intended product, 2-chloropropionaldehyde, is a thermally-unstable material. Under the conditions of such a reaction temperature and reaction time, a substantial portion of 2-chloropropionaldehyde is consumed through a consecutive reaction and the reaction yield is thus reduced. Accordingly, these processes have poor reproducibility.

Further, hydrogen chloride is by-produced through the consecutive reaction or other side reactions. It causes the materials of reactor to suffer severe corrosion and it reacts with the cobalt carbonyl catalyst to form cobalt chloride. Therefore, the processes involve problems of developing an obstacle to the reutilization of the catalyst.

In these processes, no reference is made to the separation of the product, 2-chloropropionaldehyde, from a reaction solution containing the catalyst or to the recovery and recycle of the catalyst which is important in the industrial production of 2-chloropropionaldehyde.

DISCLOSURE OF THE INVENTION

It is an object of the present invention to solve the above problems involved in the prior art processes and to provide a process for effecting efficient separation of the product, 2-chloropropionaldehyde, from a reaction solution containing the catalyst and performing the reaction stably over a long period of time upon the reutilization of the catalyst.

The above-described object of the present invention is achieved by the production process of 2-chloropropionaldehyde as described below.

In the production of 2-chloropropionaldehyde by reacting vinyl chloride, carbon monoxide and hydrogen in the presence of a rhodium compound and a base, a process for producing 2-chloropropionaldehyde which comprises maintaining the concentration of 2-chloropropionaldehyde in the liquid phase in the reaction system at not higher than 100 grams per liter of the liquid phase.

BRIEF DESCRIPTION OF THE DRAWING

The appended drawing is a flowsheet illustrating an embodiment of the present invention.

BEST MODE FOR CARRYING OUT THE INVENTION

In the production process of 2-chloropropionaldehyde of the present invention, the reaction proceeds in accordance with the following reaction formula:

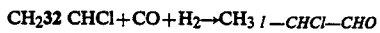

$$CH_2 = CHCl + CO + H_2 \rightarrow CH_3 - CHCl - CHO$$

In the process of the present invention, the term "base" generally signifies a Lewis base containing a Group VB element of the periodic law such as nitrogen, phosphorus or arsenic. In the absence of such a base, the rhodium compound does not exhibit any catalytic function to the aforesaid reaction.

As a preferred base useful in the process of the present invention may be mentioned, among the aforesaid bases, a base represented by the general formula $P[R^1R^2R^3]$ wherein P denotes a phosphorus atom and $R_1$, $R^2$ and $R^3$ signify individually the same or different alkyl, aryl, cycloalkyl, alkoxy, aryloxy or cycloalkoxy group, the oxide of a trivalent organic phosphorus compound, or an amine the pka of which is in the range of 3–11. It is particularly preferable that the base is a combination of a base represented by the foregoing general formula $P[R_1R^2R^3]$ and an amine the pka of which is in the range of 3–11 or a combination of the oxide of a trivalent organic phosphorus compound and an amine the pka of which is in the range of 3–11.

The amines the pka of each of which is in the range of 3–11 may generally include compounds each containing amino group(s), for example, aliphatic amines, aromatic amines, diamines, triamines, amino alcohols, amino acids, amides, urea compounds, guanidines, amidines, and nitrogen-containing compounds each of which is formed by bonding a substituent group such as an alkyl, aryl, carboxyl or hydroxyl group or a halogen atom to each nitrogen or carbon atom of the foregoing compounds and the pka of each of which is in the range of 3–11.

In addition, among heterocyclic compounds each containing one or more nitrogen atoms, compounds the pka of each of which is in the range of 3–11 are also preferred. It is particularly preferable to use at least one compound selected from pyridine compounds, quinoline compounds, imidazole compounds and morpholine compounds, the pka of each compound being in the range of 3–11.

Specific examples of the base useful in the practice of the present invention may be mentioned as follows:

The base represented by the aforesaid general formula $P[R^1R^2R^3]$ may embrace phosphines such as trimethylphosphine, triethylphosphine, tripropylphosphine, tributylphosphine, trioctylphosphine, triphenylphosphine, tricyclohexylphosphine and tribenzylphosphine, and phosphites such as trimethylphosphite, triethylphosphite, tripropylphosphite, tributylphosphite, trioctylphosphite, triphenylphosphite, tricyclohexylphosphite and tribenzylphosphite. As particular phosphines, besides those represented by the aforesaid general formula $P[R^1R^2R^3]$, may favorably be used diphosphines such as bisdiphenylphosphinomethane and bisdiphenylphosphinoethane, and phosphines bonded to crosslinking polystyrene.

The useful oxides of trivalent organic phosphorus compounds may include alkylphosphine oxides such as triethylphosphine oxide, tributylphosphine oxide and trioctylphosphine oxide, arylphosphine oxides such as triphenylphosphine oxide and tritolylphosphine oxide, and alkyl-arylphosphine oxides which contain both of alkyl and aryl groups. In addition, alkyl or arylphosphite oxides such as triethylphosphite oxide, tributylphosphite oxide and triphenylphosphite oxide, and alkyl-arylphosphite oxides which contain both of alkyl and aryl groups may be used. Further, the oxides of multidentate phosphines such as bis-1,2diphenylphosphinomethane dioxide may also be used.

The pyridine compound, quinoline compound, imidazole compound or morpholine compound, the pka of which is in the range of 3-11 is illustrated as follows:

As the pyridine compound having pka levels in the range of 3-11 may be mentioned pyridine compounds represented by the general formula:

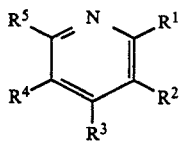

wherein $R^1$, $R^2$, $R^3 R^4$ and $R^5$ are individually a hydrogen or halogen atom, or an alkyl, aryl, cycloalkyl, hydroxyl, alkoxy, aryloxy, cycloalkoxy, carboxyl or acetyl group. Examples of such pyridine compounds may include pyridine, picoline, ethylpyridine, 2,4-lutidine, α-collidine, phenylpyridine, cyclohexylpyridine, benzylpyridine, 3-piridinol, methoxypyridine, phenoxypyridine and aminopyridine. Besides, polynuclear pyridines such as 2,2'-bispyridine may also be mentioned as other exemplary pyridine compounds.

Examples of quinoline compounds may include, besides quinoline, 2-methylquinoline, 4-methylquinoline, dimethylquinoline, 2-ethylquinoline, phenylquinoline and methoxyquinoline. In addition, various isoquinoline compounds may also be used.

On the other hand, illustrative imidazole compounds having pka levels in the range of 3-11 may be those represented by the following general formula:

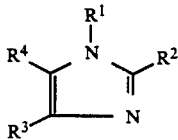

wherein $R^1$, $R^2$, $R^3$ and $R^4$ mean individually a hydrogen atom, or an alkyl, aryl, or cycloalkyl group, and $R^3$ and $R^4$ may optionally form a ring together with the 4-position and 5-position carbon atoms to form an imidazole compound with a condensed ring. As examples of such imidazole compounds, may be mentioned imidazole, N-methylimidazole, N-ethylimidazole, 2-methylimidazole, 2-ethyl-4-methylimidazole, 2-phenylimidazole, 2-undecylimidazole, N-benzyl-2-methylimidazole, 2,4,5triphenylimidazole, benzimidazole, 2-methylbenzimidazole and 2-phenylbenzimidazole.

Exemplary morpholine compounds may include N-methylmorpholine and N-ethylmorpholine in addition to morpholine.

As rhodium compounds useful in the practice of the process of the present invention, there are the oxide, mineral acid salts and organic acid salts of rhodium as well as rhodium complex compounds. Among a variety of these rhodium compounds, rhodium compounds free of any halogen are particularly preferred. As examples of such rhodium compounds, may be mentioned rhodium oxide, rhodium nitrate, rhodium sulfate, rhodium acetate, triacetylacetonatorhodium, dicarbonylacetylacetonatorhodium, dodecacarbonyltetrarhodium and hexadecacarbonylhexarhodium.

As a method for forming a halogen-free rhodium compound in the reaction system, it is possible to use a halogen-containing rhodium compound such as rhodium chloride, rhodium bromide, rhodium iodide or dichlorotetracarbonyldirhodium and then to add an alkaline compound, for example, sodium hydroxide, potassium hydroxide, potassium carbonate, trimethylamine or triethylamine in an amount equivalent or more to the halogen atom(s) of the rhodium compound to the reaction system.

In the process of the present invention, a complex compound formed of the rhodium compound and at least a part of the base may also be used more preferably. As exemplary complex compounds, may be mentioned hydridocarbonyltris(triphenylphosphine)rhodium [RhH(CO)(PPh$_3$)$_3$], nitrosyltris(triphenylphosphine)rhodium [Rh(NO) (PPh$_3$)$_3$] and η-cyclopentadienylbis(triphenylphosphine)rhodium [Rh (C$_5$H$_5$) (PPh$_3$)$_2$]. Of these various rhodium compounds, rhodium compounds which are less soluble in water are used particularly preferably in the process of the present invention. The aforementioned rhodium complex compounds such as hydridocarbonyltris(triphenylphosphine)rhodium are mentioned as an example of the particularly preferable rhodium compounds also from this point of view.

In the process of the present invention, the above-described rhodium compound may be used in an amount in the range of 0.0001–1,000 milligram atoms or preferably 0.001–100 milligram atoms in terms of rhodium atom per liter of the liquid phase in the raction system. Further, the base may be used in an amount of 0.–500 moles or preferably 0.5–100 moles per gram atom of the rhodium in the process of the present invention.

When 2-chloropropionaldehyde is produced by reacting vinyl chloride, carbon monoxide and hydrogen in the presence of the aforesaid rhodium compound and base in the process of the present invention, it is essential to maintain the concentration of 2-chloropropionaldehyde in the liquid phase in the reaction system at not higher than 100 grams per liter of the liquid phase. It is particularly preferable to keep the concentration of 2-chloropropionaldehyde in the liquid phase in the reaction system in the range of 5–50 grams per liter of the liquid phase. The "liquid phase in the reaction system" as described herein means a liquid phase containing the aforesaid rhodium compound and base and vinyl chloride used as a raw material. In the process of the present invention, the reaction may proceed without use of any reaction solvent, but generally the reaction is conducted in the presence of a reaction solvent. In this case, the "liquid phase" means a liquid phase containing the aforesaid rhodium compound and base, vinyl chloride used as a raw material and the reaction solvent. It is possible to use any reaction solvent, unless it affects the reaction adversely. The concentration of 2-chloropropionaldehyde in the liquid phase is found to exert a significant influence on the catalytic activity. Specifically, when the concentration of 2-chloropropionaldehyde is high in the liquid phase, the catalytic activity is low, whereas when the concentration is low, the catalytic activity is high. The "concentration of 2-chloropropionaldehyde in the liquid phase" means the concentration in the liquid phase in the reaction system in the course of the reaction, but it may be represented by the concentration in the organic phase directly after the reaction or, in the case of a flow reaction method, the concentration in the organic phase at the outlet of the reactor.

The present inventors found while investigating the relation of the concentration of 2-chloropropionaldehyde in the liquid phase to the catalytic activity that a sufficient reaction velocity could be obtained when the concentration of 2-chloropropionaldehyde was maintained at not higher than 100 grams per liter of the liquid phase. This value is not critical. Although the reaction may proceed even at a higher concentration than this value, the resultant insufficient reaction velocity is found to cause large disadvantages from an industrial point of view. It is preferable to control the concentration of 2-chloropropionaldehyde in the liquid phase as low as possible. However, it is difficult to maintain the concentration at an extremely low value in an industrial reaction apparatus. If this were done daringly, the volume of the reaction vessel and the amount of the recycling catalyst solution would become enormous, rather giving rise to unfavorable effects. With this point in view, the present inventors found that an industrially sufficient reaction velocity could be obtained without any need for the extremely low value when the concentration of 2-chloropropionaldehyde was maintained at 5–50 grams per liter of the liquid phase. It is particularly preferable to maintain the concentration of 2-chloropropionaldehyde at 5–50 grams per liter of the liquid phase in the process of the present invention.

A variety of methods may be used to control the concentration of 2-chloropropionaldehyde in the liquid phase in the reaction system. Among these methods are included, for example, a method of controlling the residence time of the liquid phase in a reactor and a controlling method by the continuous withdrawal of 2-chloropropionaldehyde from a reactor.

A preferred embodiment of the process of the present invention includes a process in the reaction system of which water is allowed to co-exist with a water insoluble or hardly soluble liquid medium used as a reaction solvent. The catalytic activity is further improved by means of such a process. In this case, the liquid phase in the reaction system is separated into two phases, a water phase and an organic phase. Excellent results can be obtained by maintaining the concentration of 2-chloropropionaldehyde in the organic phase at the aforesaid value, i.e., a value not higher than 100 grams or preferably in the range of 5–50 grams per liter of the organic phase.

When the reaction is carried out in accordance with such a process, it is also possible to control the concentration of 2-chloropropionaldehyde in the organic phase in the reaction system by varying the amount of water allowed to co-exist in the reaction system. Namely, a larger amount of water in the reaction system permits the concentration of 2-chloropropionaldehyde in the organic phase to be kept at a lower level. However, the co-existence of excessively large amounts of water in the reaction system is not favored in view of the volume of the reactor and the concentration of the product of 2-chloropropionaldehyde in water.

The following process is provided as a modification of the embodiment of the present invention:

A process for the production of 2-chloropropionaldehyde which comprises:

(a) reacting vinyl chloride, carbon monoxide and hydrogen in the presence of a rhodium compound, a base, a water insoluble or hardly soluble organic solvent and water to form a reaction mixture containing 2-chloropropionaldehyde, (b) separating said reaction mixture into a water phase and an organic phase, (c) separating 2-chloropropionaldehyde from said water phase so as to reduce the concentration of 2-chloropropionaldehyde therein to 5 wt. % or lower, (d) subjecting said water phase separated from 2-chloropropionaldehyde in step (c) to an anion exchange treatment to obtain regenerated water, and (e) circulating said regenerated water to step (a) to use it again together with said organic phase.

The term "a water insoluble or hardly soluble organic solvent" used in the present invention means an organic solvent which has a low degree of solubility to water. Any organic solvents may generally be used so long as their solubilities in water are 5 vol. % or lower at their application temperatures. From the industrial viewpoint, it is preferable to use an organic solvent the water-solubility of which is 0.5 vol. % of lower. Furthermore, it is particularly preferred that these solvents are stable under the reaction conditions and inert to the reaction system as well as they are capable of dissolving the rhodium compound. Hydrocarbons are preferred as such solvents. Specifically, their examples may include saturated hydrocarbons such as hexane, heptane, octane, nonane and decane, and aromatic hydrocarbons such as benzene, toluene and xylene. Mixtures of hydrocarbons, such as ligroine, kerosene, light oil and diesel oil which are available industrially, may also be included in such preferred solvents. Besides, ethers such as dipropyl ether and dibutyl ether, ketones such as diisobutyl ketone and phorone, esters such as butyl butyrate and butyl benzoate may also be mentioned as preferred solvents.

Further, in the process of the present invention, it is particularly preferable for the efficient producing of 2-chloropropionaldehyde to use a solvent which has a lower specific gravity than water as the solvent and conduct the reaction in a reactor composed of a reaction vessel equipped with a stirrer in the upper part and a gravity settling separator in the lower part while introducing water continuously in the reaction vessel in the upper part and withdrawing it continuously from the gravity settling separator in the lower part. The above-described solvents, i.e., hydrocarbons, ethers, ketones or esters may favorably be used also in this case because all of them have smaller specific gravities than water.

The stirrer used in the above-described reactor may be used in any of its style so far as it has a function of efficient mixing and stirring of the reaction solvent, water, and carbon monoxide and hydrogen. The gravity settling separator is only satisfactory if it is able to separate the reaction solvent from the water. The separator should preferably have a enough diameter, so that the water goes down at such a speed as not to accompany small droplets of the solvent produced by the stirring.

In the process of the present invention, no particular limitation is vested on the amount of water to be allowed to exist during the reaction. However, the effect of water will be reduced when water is added in an extremely small amount. On the contrary, the use of excessively large amounts does not improve reaction results beyond a certain level. Usually, the amount of water may preferably be in the range of 0.01–1,000 in terms of its weight ratio to vinyl chloride which is to be fed as a raw material to the reactor. It is particularly preferable to add water at a weight ratio in the range of 0.1–100.

When the base to be used in the present invention is soluble in water, it is also preferable to supply the base as a solution having at least a part of it dissolved in the water to be fed to the reaction system. For example, when imidazole is used as the base, it is preferable to supply it to the reactor in the form of an aqueous imidazole solution.

In the process of the present invention, the reaction product, 2-chloropropionaldehyde, is taken out of the reaction system preferably in the form of a solution having its greater portion dissolved in the water phase. In this case, it is easy to separate 2-chloropropionaldehyde from the water phase, for example, by conventional distillation or extraction operation. With distillation, the distillation temperature should preferably be as low as possible in view of the thermal stability of 2-chloropropionaldehyde so that the distillation is generally carried out at temperatures in the range of 40°–90° C. It is important in the separation of 2-chloropropionaldehyde to reduce the concentration of 2-chloropropionaldehyde remaining in the water phase to not higher than 5 wt. %. This is due to the fact that since a small amount of rhodium component is dissolved in the water phase, the loss of rhodium to the outside of the reaction system can not be ignored if the water phase is not utilized repeatedly. In this case, it is important to control the concentration of 2-chloropropionaldehyde in the catalyst-containing organic phase in the reaction system at not higher than 100 grams per liter of the organic phase in order not to reduce the catalytic activity, upon the circulation of the water phase to the reactor. Accordingly, it is preferable to reduce the concentration of 2-chloropropionaldehyde in the water phase as far as possible and particularly preferable to lower it to 1 wt. % or less if possible.

The water phase thus-obtained is circulated to the reactor and used repeatedly. However, its use for a long period of time causes a variety of by-products and impurities in the raw material to be accumulated. In these by-products and impurities are involved matters which degrade the catalytic activity. Particularly, anions such as chlorine ions and sulfide ions are found to deteriorate the catalytic activity seriously. The present inventors observed a practically complete removal of matters having such activity-degrading effects to the outside of the system by subjecting the water phase to an anion exchange treatment as a method of removing those matters degrading the catalytic activity. The anion exchange treatment is effected by any conventionally prevailing anion exchange methods, for instance, by a method in which the water phase is allowed to flow through a column packed with anion exchange resins.

Either of strongly basic anion resins or weakly basic anion resins may be used as the anion exchange resins. The selection should however be made taking the removal efficiency of these anions and the regeneration cost into account. In addition, methods utilizing ion exchange membranes or employing ion exchange liquors may be mentioned as illustratives of the anion exchange treatment.

The concentration of anions remaining in the regenerated water obtained by the anion exchange treatment should preferably be as low as possible. However, a little amount of anions is permitted to remain in the water. Generally, little influence is exerted on the reaction when the concentration of total anions is not more than 50 milliequivalents per liter of the regenerated water.

In the practice of the process of the present invention, another component, e.g., an additive for the improvement of the stability of the rhodium catalyst or an additive for the improvement of the activity and selectivity of the catalyst, for example, a carboxylic acid may coexist in the reaction system without any particular obstacles. When these additives are soluble in the water phase, it is necessary to pay attention so that these useful components are not removed to the outside of the system by the proper selection of anion exchangers for use in the anion exchange treatment of the water phase.

The process of the present invention is usually carried out at a reaction temperature of 20°–150° C. and at a reaction pressure of 1–200 kg/cm gauge or preferably 20–120 kg/cm$^2$ gauge. The lower the reaction temperature, the better in view of the thermal stability of the resulting 2-chloropropionaldehyde. For this reason, 20°–100° C. is a particularly preferred temperature range. The mixing molar ratio of carbon monoxide to hydrogen, both of which are used as raw materials, may generally fall within the range of 10–0.1 or preferably 4–0.2. Carbon monoxide and hydrogen may thus be provided as a mixed gas which contains the both components at the aforementioned composition ratio. Water gas may thus be used either as is or as a mixture with a gas inert to the reaction such as methane or nitrogen or with carbon dioxide. The other raw material, vinyl chloride, may be used in a gaseous or liquid form or in the form of a solution having it dissolved in a solvent which is used for the reaction. Although no particular limitation is imposed on the amount of the mixed gas of carbon monoxide and hydrogen used as raw materials, it is preferable to use it in an amount equivalent or more to the vinyl chloride used.

It is not necessary to vest any particular limitations on the temperature of the anion exchange treatment. It is however favorable to conduct the treatment at lower temperatures from the view point of the thermal stability of the anion exchangers used. The treatment is carried out at temperatures in the range of from room temperature to 60° C.

The process of the present invention may be practiced in accordance with any one of the batch, semi-batch or continuous process.

In the case of the batch process for example, vinyl chloride is added in a gaseous or liquid form or as a solution to an autoclave in which a rhodium compound, a base, optionally a reaction solvent and water have been charged. A gas containing carbon monoxide and hydrogen is then introduced into the autoclave to a predetermined pressure. By heating the autoclave preferably under stirring, the reaction is allowed to proceed. The thus-obtained reaction mixture is thereafter left at rest, so that it is separated into a water phase and an organic phase. The organic phase is again charged for its reutilization into the autoclave, after being added with water or in some instances, water and a base or an aqueous solution containing the base, as required. On the other hand, the water phase is subjected to a desired separation operation such as distillation or extraction so as to separate the intended reaction product, 2-chloropropionaldehyde, from the water phase. The concentration of 2-chloropropionaldehyde in the organic phase can be controlled and maintained at a value in a preferred range by changing the ratio of water to the organic phase, the reaction time, and the amount of the reaction solvent.

In an exemplary continuous process, the reaction is carried out by charging a rhodium compound, a water insoluble or hardly soluble organic solvent, and optionally a base into a pressure tight reaction vessel in advance, feeding continuously water or optionally an aqueous base solution to the reaction vessel at its upper part and the raw materials, i.e., vinyl chloride, carbon monoxide and hydrogen to the reaction vessel at its lower part under stirring, and discharging continuously the water phase containing the reaction product, 2-chloropropionaldehyde, from the lower part of a gravity settling separator provided below the reaction vessel.

Then, the water phase is preferably treated in a distillation apparatus operated under a subatmospheric pressure to separate substantially all of the reaction product, 2-chloropropionaldehyde. The resulting water phase is made practically free of the anions contained therein in an anion exchange apparatus and then circulated to reaction vessel for its reutilization.

In accordance with the process of the present invention, 2-chloropropionaldehyde can be produced from vinyl chloride, carbon monoxide and hydrogen used as raw materials at lower temperatures and pressures than in the conventional processes.

Particularly, in accordance with the process of the present invention, it becomes possible to continue the reaction by using a catalyst repeatedly for a prolonged period of time while maintaining its catalytic activity at a higher level than conventionally attainable.

The present invention is illustrated more specifically with reference to the following Examples.

EXAMPLE 1

A reaction vessel (material: SUS 316, inner diameter: 30 mm, height: 450 mm, actual volume: about 300 ml) with a pressure resistance of 200 kg/cm$^2$ gauge and equipped with a 7-stage-impeller stirrer and a hot water jacket was maintained at a temperature of 60° C. and a pressure of 60 kg/cm$^2$ gauge. Into the reactor were continuously charged a rhodium catalyst solution [an orthoxylene solution containing 20 mmols of hydridocarbonyltris(triphenylphosphine)rhodium, 40 mmols of triphenylphosphine, 5.6 g of 2-chloropropionaldehyde and 32 mmols of imidazole per liter], an aqueous imidazole solution (containing 1 mol of imidazole per liter), vinyl chloride and a 1:2 (molar ratio) mixed gas of carbon monoxide and hydrogen at respective feed rates of 1,200 ml/hour, 300 ml/hour, 2.2 mols/hour and 320 l/hour through an inlet nozzle provided at the lower part of the reaction vessel. At the same time, a liquid reaction mixture comprising a water phase and an organic phase, unreacted vinyl chloride and carbon monoxide and hydrogen were discharged continuously through an outlet nozzle provided at the upper part of the reaction vessel to a gas-liquid separator operated at 45° C. under the same pressure as in the reactor.

In the gas-liquid separator, a large part of unreacted vinyl chloride and carbon monoxide and hydrogen was taken out from a gas outlet nozzle provided at the upper part of the separator and sent to an unreacted gas holder maintained at atmospheric pressure via a pressure control valve. On the other hand, the liquid reaction mixture was withdrawn through a liquid outlet nozzle provided at the lower part of the gas-liquid separator and sent to a gravity settling separator operated at atmospheric pressure via a liquid level control valve. In the separator, the liquid reaction mixture was separated into an upper organic phase (xylene layer) and a lower water phase. In the organic phase was contained 35 g of 2-chloropropionaldehyde, which was extracted with 500 ml of water, whereby the content of 2-chloropropionaldehyde was reduced to 6.7 g. This solution had practically the same composition as the rhodium catalyst solution described above and was used again by mixing it with a rhodium catalyst solution supplied to the reaction vessel. Separately, the water phase was mixed with the aforesaid water which contained the 2-chloropropionaldehyde extracted and the resulting mixture was charged intermittently to and distilled in a batch-type distillation apparatus kept at a pressure of 500 mmHg, a bottom temperature of 70° C. and a top temperature of 60° C. in an amount of about 3,500 ml, i.e., the combined amount of 4-hour production. About 30 ml of initial fraction was cut off for every batch of distillation and the components distilled out at a top temperature of 60° C. were collected entirely. For every batch of distillation, 3,500 g of an aqueous solution containing 1,185 mmols of imidazole was obtained on an average as a residue of the vacuum distillation. In the solution were contained about 320 mmols of chlorine ions and 1.8 g of propionic acid as impurities. By removing the chlorine ions in the residue by an ion exchange method, 800 ml of an aqueous solution containing 296 mmols of imidazole was obtained per hour on the average. The aqueous solution was concentrated under atmospheric pressure through evaporation and adjusted in volume at 296 ml. Then, it was mixed with the aqueous imidazole solution to be sent to the reaction vessel for its reutilization.

A continuous operation was carried out over 24 hours in the manner as described above. The distillate from the vacuum distillation apparatus was 2-chloropropionaldehyde containing 10.4% of water on average, and its amount produced per hour became practically constant within the range of about ±5.6% at about the 7th hour after the initiation of the operation and was kept practically constant until the 24th hour thereafter. During 4 hours from the 16th hour to the 20th hour after the initiation of the reaction, 107 g of 2-chloropropionaldehyde containing 10.4 wt. % of water was obtained per hour on average.

COMPARATIVE EXAMPLE 1

The reaction was carried out in the same manner as in Example 1 except that an orthoxylene solution containing 30 mmols of hydridocarbonyltris(triphenylphosphine)rhodium, 60 mmols of triphenylphosphine, 8.4 g of 2-chloropropionaldehyde and 36 mmols of imidazole per liter was used at a rate of 150 ml per hour as the rhodium catalyst solution to be fed to the reaction vessel and an aqueous solution containing 3 mols of imidazole per liter was used at a rate of 100 ml per hour as the imidazole solution to be fed to the reaction vessel in the procedure of Example 1. Upon an elapsed time of 12 hours after the initiation of the reaction, the total system reached practically a steady state. The concentration of 2-chloropropionaldehyde in the organic phase at the outlet of the reaction vessel at this moment was 184 g per liter of the solution. The product, 2-chlororpopionaldehyde, taken out of the distillation system contained about 10.6% of water and its amount was 56 g per hour on average.

EXAMPLE 2

Referring to the appended drawing, into a reaction vessel 1 [material: SUS 316 L, inner diameter: 25 mm, height: 350 mm, actual volume: about 170 ml, provided with a gravity settling separator 2 having an inner diameter of 25 mm and a height of 150 mm in the lower part thereof] having a pressure resistance of 100 kg/cm² gauge and equipped with a 10-stage-impeller stirrer and a hot water jacket were charged 1 mmol of hydridocarbonyltris(triphenylphosphine)rhodium, 5 mmols of triphenylphosphine and 50 ml of toluene as a reaction solvent. Then, 17.5 g /hour of vinyl chloride and about 4 l/hour of a 1:2 (molar ratio) mixed gas of carbon monoxide and hydrogen were charged continuously into the reaction vessel through respective inlet nozzles 11 and 12 provided at the lower part of the reaction vessel 1 under the conditions of a reaction temperature of 50° C. and a reaction pressure of 75 kg/cm² gauge. At the same time, an aqueous imidazole solution having 15 g of imidazole dissolved in a liter of the solution was charged thereto at a rate of 150 g/hour through a conduit 19 and a liquid inlet nozzle 20 provided at the upper part of the reaction vessel from an aqueous imidazole solution tank 6.

A liquid outlet nozzle 13 was mounted at the bottom of the gravity settling separator 2 provided under the reaction vessel, and a water phase consisting of an aqueous imidazole solution containing the reaction product, 2-chloropropionaldehyde, was taken out of a reactor [comprising the reaction vessel 1 equipped with a stirrer in the upper part and the gravity setting separator 2 in the lower part] continuously through the liquid outlet nozzle 13 so as to maintain the liquid level in the reaction vessel constant. On the other side, unreacted vinyl chloride and a gas containing unreacted carbon monoxide and hydrogen were continuously withdrawn from a gas outlet nozzle 18 provided at the top of the reaction vessel so as to maintain the pressure within the reaction vessel 1 constant. It was confirmed that small amounts of chlorine ions (presumably as imidazole hydrochloride) and propionic acid and rhodium in a concentration of 1.8 ppm were present in the water phase, in addition to imidazole and 2-chloropropionaldehyde. Subsequently, the water phase was treated in a glass-made batch-type distillation apparatus 3 operated at a pressure of 50 mmHg and a bottom temperature of 60° C. so that it was separated from the greater part of 2-chloropropionaldehyde and recovered through a bottom liquid outlet nozzle 15 as an aqueous solution containing 1.5 wt. % of 2-chloropropionaldehyde. Through a distillate outlet nozzle 14 of the batch-type distillation apparatus 3, 2-chloropropionaldehyde (containing 10.2 wt. % of water) was obtained in an amount of 7.2 g per hour.

On the other hand, the water phase was passed through a glass column 4 packed with 1,000 ml of a strongly basic anion exchange resin (trade name: Lewatit M500) which had been regenerated to its OH-active form via a conduit 15, whereby chlorine ions and propionic acid were removed. The water phase was recovered through a liquid outlet nozzle 16 into a regenerated water tank 5 as regenerated water. It was confirmed that the concentrations of the residual chlorine ions and propionic acid in the regenerated water were individually not higher than 5 milliequivalents per liter while the rhodium concentration was constant within the error range of analysis. The regenerated water was circulated to the reaction vessel again via a conduit 17 and a liquid inlet nozzle 20 for its reutilization.

A continuous operation was carried out over 72 hours in the manner as described above. The distillate from the batch-type distillation apparatus 3 was 2-chloropropionaldehyde containing 10.4% of water on average, and its amount produced per hour became practically constant within the range of about ±10% at about the 5th hour after the initiation of the operation and was kept practically constant until the 72nd hour thereafter. During 4 hours from the 68th hour to the 72nd hour after the initiation of the reaction, 7.4 g of 2-chloropropionaldehyde containing 10.4 wt. % of water was obtained per hour on average.

What is claimed is:

1. In a continuous process for producing 2-chloropropionaldehyde, comprising the steps of:
    (a) reacting vinyl chloride, carbon monoxide and hydrogen in the presence of a rhodium compound, a base, a water insoluble or barely soluble organic solvent and water at a temperature of 20° to 150° C. and a pressure of 1 to 200 kg/cm² to obtain a reaction mixture containing 2-chloropropionaldehyde.
    (b) separating said reaction mixture into a water phase and an organic phase,
    (c) separating and obtaining 2-chloropropionaldehyde from said water phase so as to reduce the concentration of 2-chloropropionaldehyde in said water phase to not higher than 5 weight percent,
    (d) subjecting said water phase separated from 2-chloropropionaldehyde in step (c) to an anion exchange treatment to obtain regenerated water, and
    (e) circulating said regenerated water to said step (a) to use it repeatedly together with said organic phase, the improvement wherein said solvent has a specific gravity lower than that of water and the reaction is carried out in a recorder composed of a reaction zone equipped with a stirrer in the upper part and a gravity settling separation zone provided beneath said reaction zone while continuously withdrawing said water phase containing the resulting 2-chloropropionaldehyde from the lower part of the gravity settling separation zone to continuously circulate said water phase to the upper part of said reaction zone after being subjected to said steps (c) to (e).

* * * * *